Figure 1:
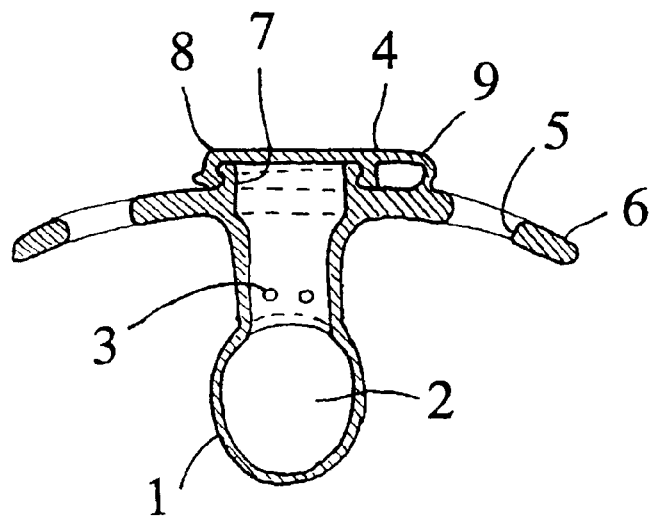

United States Patent
Aaltonen et al.

[11] Patent Number: 6,126,678
[45] Date of Patent: Oct. 3, 2000

[54] INTRAORAL ADMINISTRATION DEVICE

[76] Inventors: Antti Sakari Aaltonen, Marttilantie 2 as. 6, Pusula, Finland, FIN-03850; Jouko Suhonen, 663 Garth Ct., Yorktown Heights, N.Y. 10598

[21] Appl. No.: 09/297,939
[22] PCT Filed: May 22, 1998
[86] PCT No.: PCT/FI97/00682
   § 371 Date: Jul. 2, 1999
   § 102(e) Date: Jul. 2, 1999
[87] PCT Pub. No.: WO98/20809
   PCT Pub. Date: May 22, 1998
[30] Foreign Application Priority Data Nov. 11, 1996 [FI] Finland ................... 960558 U

[51] Int. Cl.⁷ ........................................... A61J 17/00
[52] U.S. Cl. ..................... 606/234; 606/236; 604/77
[58] Field of Search ....................... 606/234, 235, 606/236; 604/53, 54, 73, 77, 234–236; D24/194

[56] References Cited

U.S. PATENT DOCUMENTS

| | | | |
|---|---|---|---|
| 5,127,903 | 7/1992 | Mailot et al. | 604/77 |
| 5,395,392 | 3/1995 | Suhonen | 606/234 |
| 5,512,047 | 4/1996 | Dvorak | 606/234 |
| 5,514,142 | 5/1996 | Dean-Homolka | 606/234 |
| 5,772,685 | 6/1998 | Crowe et al. | 606/234 |

Primary Examiner—Gary Jackson
Attorney, Agent, or Firm—Evenson, McKeown, Edwards & Lenahan, P.L.L.C.

[57] ABSTRACT

The invention relates to an administration device for a method to prophylactically treat the mouth region of children, comprising a part intended to be positioned in the mouth, which part is provided with a dispensing container for an active agent, and having at least one aperture allowing the entrance of saliva into the dispensing container and its exit therefrom, and a part to remain outside the mouth, comprising a hand held member, whereby a filler opening concentrically opening towards the hand held member, is arranged in the area between both parts. The invention is characterized in that the hand held member and a cover of the filler opening, which cover is an integral part of the hand held member, are manufactured as one uniform unit with the rest of the administration device.

20 Claims, 2 Drawing Sheets

INTRAORAL ADMINISTRATION DEVICE

The object of the present invention is an intraoral administration device according to the preamble of claim 1, by means of which it is possible to provide a local therapeutic effect in the region of the mouth and throat, which device is adapted to take into account the eruption order of the teeth and the location of the salivary glands, while simultaneously satisfying the physiological sucking need and craving for sweetness of small children, using small dosage levels tolerated by children and without causing malocclusions.

The administration device is characterized in that the development of a child is taken into account by providing for each development phase an individual device type, the construction of which and the location of the dispensing containers are adapted to take into account the eruption order of the teeth and the optimal function of the developing occlusion organ.

J. Suhonen (1992) has in his article "Mutans streptococci and their specific oral target. New implications to prevent dental caries" in the Swiss Journal "Schweiz Monatsschrift Zahnmed", 1992, 102, 286 to 291, presented the theoretical background for the use of a pacifier-type admistration device which slowly releases an active agent into the mouth, in a prophylactic method for the prevention of dental caries. The operability of a dispensing pacifier in vitro has been presented in the article "Realease of preventive agents from pacifiers in vitro" by J. Suhonen et. al. in said Swiss Journal "Schweiz Monatsschrift Zahnmed", issue 1994, 104, 946 to 51.

A dispensing pacifier prototype for dispensing sodium fluoride, xylitol and sorbitol has in our field trial in the health centre of the district of Lohja with children of an age of 16 months proved to be a functioning means with potential for development for the treatment of diseases of the mouth and the throat of children in the sucking-age. There appeared a significant reduction in dental caries and otitis in children using a dispensing pacifier, compared with children to whom the same prophylactic agent was administered without a pacifier.

Most of the known dispensing pacifiers, such as "Unit-dosing nipple" disclosed in U.S. Pat. No. 4,078,566, J. J. Urban, "Teething dummy" described in GB-patent application 2 181 957, K. Needham, a pacifier according to European patent application 0 494 904 and FI-patent application 921411, developed by J. Suhonen, as well as CANNON babysafe Minifeeder, available in pharmacies, consist of at least three parts detachable from each other, i.e. a sucking piece, a cover and a protecting plate arranged between them, or a mounting ring provided with a thread, for a cover/bottle. This solution is either injuriously massive for the teeth (Urban, Needham, CANNON), or as to the manufacturing technique too exacting (as to the technique of locking of the cover and the sucking piece of the pacifier developed by Suhonen), or too complicated. However, the greatest problem related to these devices is that if the device is not closed correctly due to human carelessness, a releasing part may fall into the throat of a child and cause danger of suffocation.

In a dispensing pacifier according to U.S. Pat. No. 5,127,903, Mailot et. al., a protecting plate and a sucking piece are integrally formed, but it is characterized in that the interior of the sucking piece is divided into compartments and to a separate chamber for receiving a removable medicament containing unit. The solution of this kind is unhygienic, as in the connection with the cleaning of the sucking piece, it is difficult to wash off the saliva entered into the sucking piece.

It is the primary object of this invention to provide such an intraoral administration device in which the above mentioned drawbacks have been overcome and which is safe in use without any releasing parts endangering the safety. This aim has been achieved by an administration device according to the characterizing part of claim 1.

The intraoral administration device according to the present invention consists of a part intended to be positioned in the mouth, comprising a dispensing container for an active agent, which is provided with at least one aperture allowing the entrance of saliva into the container and its exit therefrom, and a part remaining outside the mouth, comprising a hand hold member, whereby a filler opening which opens centrically towards the hand hold member, is arranged in the area between both parts. The hand hold member of the administration device and a cover of the filler opening, which cover is integrally formed with the hand hold member, are manufactured as one uniform unit with the rest of the adminstration device, whereby the adminstration device does not comprise any releasing pieces. The hand hold member can be knob or ring shaped.

In the construction and in the selection of the materials of this administration device, the requirements determined by the Comite Europeen de Normalisation (CEN) for the standard of pacifiers, have been tried to take into consideration to the extent appropriate. As the sucking piece of the administration device is not empty, but contains an active agent, it cannot, however, be regarded as a conventional pacifier, but as a dispenser developed from a feeding bottle. According to the CEN safety standards, a protecting plate is provided with air holes. The administration device is in its entirety preferably manufactured from an elastic material, such as rubber, silicone or soft vinyl.

According to an advantageous embodiment of the administration device, a filler opening of a dispensing container, which filler opening is arranged in the part remaining outside the mouth, is wide and outwardly widening in shape, in order to facilitate the cleaning and drying through the same, and the edge of the filler opening is bottle mouth shaped. The cover of the filler opening is integrally formed with the hand hold member and is closable with an elastic cap, which is permanently connected to the administration device by means of a joining strip. In a closed position, the extensible edge of the cover can be snapped over the bulged edge of the filler opening. The cover, constructed to close tightly, serves simultaneously as a gripping means of the administration device, and an approvable tether can be attached to the joining strip thereof. Although the cover of the pacifier-type administration device can, in an open position, extend outside the edge of the protecing plate, depending on the location of the joining strip, this does not cause any risk in the normal use, as the cover is always in the closed position during the use of the administration device.

According to another embodiment, a cover is connected to a ring-shaped hand hold member, whereby said cover, even in an open position, does not extend outside the edge of the protective plate of the pacifier-type administration device. In this embodiment, the points joining the ring-shaped hand hold member with the rest of the administration device, are located on the opposing sides of the filler opening in a suitable distance from each other and the cover of the centrically positioned filler opening is connected to the sides of the ring-shaped hand hold member by means of at least two closing shafts, arranged in a substantially V-shaped manner with respect to each other. So the cover is integrally formed with the hand hold member construction by using the elasticity of the construction. In order to facilitate the opening and the closing of the cover, a gripping means is preferably arranged close to the area joining the closing shafts and the cover. By shaping the sides of the ring-shaped hand hold member inwardly curved, said sides including points joining each closing shaft with the hand hold member, a construction is achieved which advantageously contributes to secure the cover to remain in place in the closed position.

In an alternative embodiment, a cover can also be formed by a plug entering into a filler opening like a bottle plug, and it can be provided with a ¼ thread or a bayonet attachment. In the design with a ring-shaped hand hold member, the elastic closing shafts are sufficiently expandable when opening and closing the cover of this kind. In the closed position of the cover, the closing shafts prevent the cover plug from being unscrewed by itself. In the embodiment with a knob-shaped hand hold member, the plug-shaped cover entering into the filler opening, can also be opened by prizing, using a suitable key in a recess provided in the cover.

To prevent malocclusions Varrela and Alanen have in their article "Voidaanko hampaiden asentovirheitaehkäistä?" (Can displacements of the teeth be prevented?), Suom. Hammasl. Lehti, 1995, No. 17, 951–4, presented an extensive pacifier study with an aim at finding a pacifier design which broadens the dental arch of the upper jaw. In the dispensing pacifier according to the present invention, this aim can be achieved by means of a laterally flattening sucking piece, into which an active agent can practically be dosed. The sucking piece is provided with one or more apertures allowing the entrance of saliva into the sucking piece and the exit of an active agent dissolved in saliva therefrom. According to an advantageous embodiment the shaft of the sucking piece is provided with four apertures, two of which facing the upper jaw and two facing the lower jaw.

In the continuous follow-up of our study cohort, it has been established that malocclusions in children using a pacifier become significantly more common when the use of the pacifier continues beyond the age of two. For this reason, taking into account the individual dentoalveolar jaw development, the pacifier shoud be given up at the stage of eruption of the deciduous molars which, on an average, coincides with that age, at which stage the sucking need of a child optimally should already have changed into a chewing-need. Prolonged pacifier sucking has also been alleged to cause middle ear infection. On the other hand, if the pacifier is taken away from a child too early, he easily becomes a thumb-sucker which, from the point of view of bite development, is an even worse habit than sucking a pacifier. Also deciduous dentition destroyed by early caries attack cause displacements and malocclusion of the permanent teeth. A common reason for early caries is feeding children from a nipple bottle with juices sweetened with sugar, especially if this happens during bed time. During sleep salivation ceases, and the juice being sucked into the mouth, remains for a long time around the teeth serving as a most effective nutritive medium for teeth destroying bacteria. Suhonen et al. found out that the destroying mechanism of caries caused by a feeding bottle, can be converted into a protecting mechanism when, instead of fermentable liquids, unfermentable liquids, such as fluoride and xylitol, are administered to a child from a pacifier used in the night or prior to falling a sleep. In a study of Uhari et al. "Xylitol chewing gum in prevention of acute otitis media: double-blind randomized trial", published in the British Medical Journal 1996, 313, 1180–1184, it has been established that the use of xylitol has also reduced infection of middle ear in nursery children regularly using a full xylitol bubble gum. However, acute middle ear infection appears most commonly in children under the age of two, at which age the use of a bubble gum is problematic. In addition, in the bubble gum study, the used amount of xylitol (8,4 g/day) is too large to be used for small children as it can cause osmotic diarrhea.

A dispensing pacifier according to the present invention is used as an administration device for prophylactic agents for children in the sucking age under the age of two. By means of the pacifier, used prior to falling a sleep, a sustained local effect is obtained in the region of the mouth and throat. For example, a sufficient daily amount of xylitol, administered in the connection with afternoon nap or night sleep, is less than 0.5 g which dose is tolerated by the stomach of children even under the age of six months. The agent to be dispensed from the sucking piece of the pacifier, must be of a soft consistency (in the form of a gel, a powder or a fine granular) in order to eliminate the risk of a hard tablet to fall into the throat of a child if the sucking piece is broken due to biting the sucking piece against a hard tablet. Sucking pieces are generally manufactured of silocone, rubber or soft vinyl. Many children already having teeth, will break a sucking piece, especially such one made of silicone, in a short time by biting. On the other hand, pacifiers made of rubber, will cause a greater risk of allergy. For hygienic reasons, it is in any case recommended to replace a pacifier by a new one at least once a month, or immediately when a breakage of the pacifier is observed. If a child repeatedly breaks the sucking piece by biting, it is recommended to use an administration device without a sucking piece.

According to the invention, an administration device of an oral screen type has now been developed, in which a dispensing container is placed in a central region of the oral screen intended to be hold in the space between the lips and the teeth, so that prophylactic agents, e.g. specific antibodies preventing the colonization of bacteria, are released onto the labial surfaces of the front teeth, which during the first year of the eruption of the deciduous teeth are exposed to the greatest danger to be colonized by a caries causing microbial flora. A small child can be pursued to use an elastic oral screen, instead of a pacifier, by using the natural craving for sweetness of a small child. As sweetening agents, such agents are used which are safe for the teeth, e.g. xylitol which also will prevent infections by caries and otitis bacteria during long term use. The first times the adminstration device is offered, the sweetening agent have to be moistened with water in order to enable dissolved agent to flow immediately from the container into the mouth of a child. The taste buds in the tongue tip of a child are very sensitive to sweet, and the taste sensation leads immediately to an increased salivation from glands under the tongue. This saliva can flow freely through one or more apertures, provided in the inner surface of the oral screen, into the dispensing container in which the saliva continues slowly dissolving a tablet introduced therein through the filler opening arranged in the outer surface of the oral screen. According to the invention, a cover of the filler opening is integrally formed with the hand hold member construction, and is constructed analogously to the closing mechanism presented above in the connection with the dispensing pacifier with a ring-shaped hand hold member. When pressing the ring from the sides, the closing shafts push the cover towards the dispensing container. In this way it is also possible initially to pump the dissolved sweetening agent into the mouth of a child which helps the child to approve the device. The device can preferably be manufactured from a strong teether material, and the bail of the hand hold member thereof can be moulded suitable for chewing. For a child in the age of the eruption of teeth, the device can thus serve as a teether, when the child is awake, and as an oral screen prior to falling a sleep. The oral screen dispenser does not cause displacements of the teeth as a pacifier does. By preventing mouth breething, it can also reduce the risk of otitis.

By a correct design of the sucking piece of a dispensing pacifier too, it will be possible to prevent malocclusions, especially crossbites in children using the pacifier. Because of the purpose of the use of such a dispensing pacifier, it is usually taken into use not until an age of 3 to 6 months. In order to help a child to accept a dispensing pacifier which has been designed taking the orthodontic prophylaxis point of view into account, the child should already at the maternity hospital be given a pacifier/training pacifier having the shape of the dispensing pacifier but having no apertures on its sucking piece.

Figure 2:
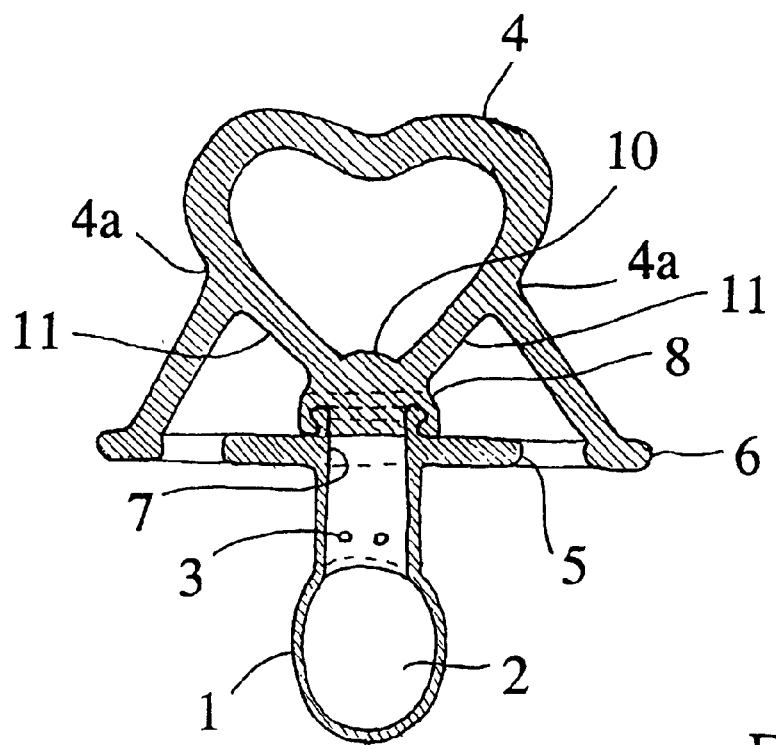
Figure 3:
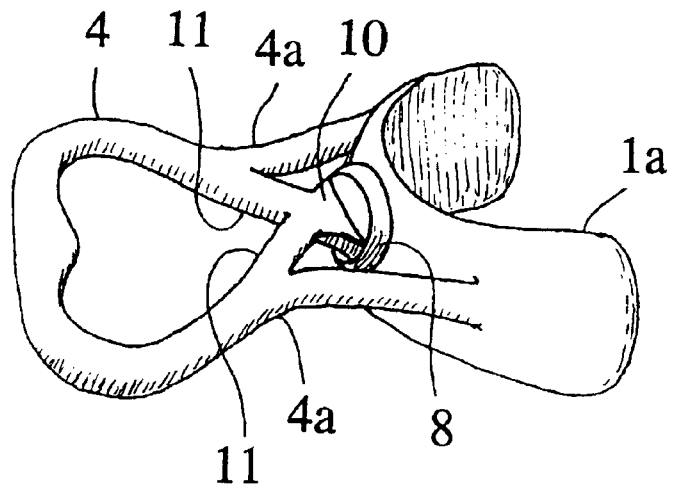
Figure 4:
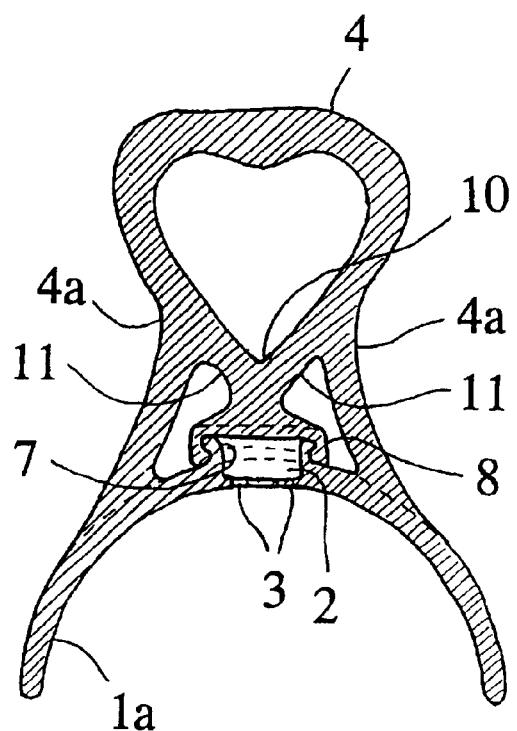

In the following the intraoral administration device according to the invention will be described more in detail with reference to the drawings in which FIG. 1 illustrates an embodiment of a pacifier-type administration device according to the invention, provided with a knob-shaped hand hold member, as a horizontal longitudinal cross-section, FIG. 2 illustrates another embodiment of a pacifier-type adminstration device according to the invention, provided with a ring-shaped hand hold member, as a horizontal longitudinal cross-section, FIG. 3 illustrates a perspective view of an embodiment of an adminstration device of the oral screen type according to the invention, and FIG. 4 illustrates the adminstration device shown in FIG. 3 as a horizontal longitudinal cross-section.

In the first embodiment of the invention, shown in FIG. 1, the adminstration device manufactured as a one piece device, is a pacifier comprising, as a part to be positioned in the mouth, a sucking piece 1, the interior of which forms a dispensing container 2 for an active agent. The sucking piece 1 is provided with at least one aperture, through which saliva can enter into the dispensing container 2 and flow out therefrom simultaneously bringing dissolved active agent with it. The location of the apertures 3 is chosen so that the active agent flowing through the apertures, will come directly into contact with the erupting teeth. The sucking piece 1 of the dispensing pacifier shown in FIG. 1, is preferably laterally flattening in shape, whereby a flatten shaft of the sucking piece is provided with four apertures 3, two of which facing the upper jaw and two facing the lower jaw so that the saliva secreted from the submandibular and sublingual salivary glands can freely flow into the sucking piece 1 serving as a dispensing container 2, and out therefrom, bringing the active agent dissolved in the saliva around the front teeth. A part remaining outside the mouth comprises a hand hold member 4 and a protecting plate 6, which is provided with air holes 5. The protecting plate 6 can be slightly curved as shown in FIG. 1. The protecting plate 6 includes a filler opening 7 of the dispensing container 2 which opens centrically towards the hand hold member 4. The hand hold member 4 and the cover 8 of the filler opening, which cover 8 is an integral part of the hand hold member, are manufactured as one uniform unit with the rest of the adminstration device.

The administration device shown in FIG. 1 has a knob-shaped hand hold member 4, the main part of which forming a cap-shaped cover 8. The filler opening 7 of the dispensing container 2 is slightly outwardly widening in shape, and the edge of the filler opeinig is bottle mouth shaped. The elastic cap-shaped cover 8 is connected to the administration device by means of a flexible joining strip 9. For closing the filler opening 7, the cap-shaped cover 8 can be snapped over the bulged edge of the filler opening 7.

The cover 8 can also be constructed as a plug entering into the filler opening 7, the outer surface of the cover plug being provided e.g. with a recess for a key in order to facilitate the opening of the cover 8. The mantle surfaces of the cover 8 and the filler opening 7 may be provided with cooperating ¼ threads, or with a bayonet attachment.

FIG. 2 shows another pacifier-type administration device, in which the sucking piece 1 is substantially analogous to that of the foregoing embodiment. In this embodiment, the protecting plate 6 is substantially planar. The dispensing pacifier is moulded of silicone to one piece, and comprises a sucking piece 1, a protecting plate 6, and a ring-shaped hand hold member 4, which is connected to the protecting plate 6 close to the outside periphery thereof. The dispensing container 2 is filled by removing a cover 8, which is an integral part of the hand hold member 4, from the filler opening 7 either by pushing or by unscrewing while gripping a gripping means 10, whereby V-shapedly extending closing shafts 11 connecting the cover 8 to the ring-shaped hand hold member 4, which closing shafts joint to the ring-shaped hand hold member by means of joints arranged at inwardly curved sides 4a thereof, are resiliently pushing the sides 4a outwards. For the time of filling, the cover 8 can be pushed sidewards and when the filling has been carried out, the cover 8 can again be placed onto the filler opening 7, whereby the closing shafts facilitate the closing of the filler opening 7. The protecting plate 6 is preferably provided with four air holes 5. To secure the closing of the cover 8, the cover may be provided with a ¼ thread or a bayonet attachment of the same type as in the dispensing pacifier with a knob-shaped hand hold member.

In the adminstration device shown in FIGS. 3 and 4, the part to be positioned in the mounth, comprises an oral screen 1a intended to be hold in the space between the lips and teeth. The dispensing container 2 is placed in the central region of the oral screen 1a, whereby the apertures 3 provided in the dispensing container open towards the labial surfaces of the front teeth. The con20 structions of the cover 8 to close the filler opening 7 of the dispensing container 2 and the hand hold member 4 correspond substantially to the solutions shown in FIG. 2. Due to the construction of the ring-shaped hand hold member 4 and the elasticity of the whole admintration device, the active agent, introduced in the dispensing container 2, can be exposed to pumping effect by pushing the sides of the ring-shaped hand hold member 4 towards each other.

The administration device can be shortly boiled in order to meet the requirements of the hygienic standard under domestic conditions.

For a person skilled in the art it is evident that the invention is not restricted only to the examples shown above, but can vary within the scope of the appended patent claims.

What is claimed is:

1. Administration device for a method to prophylactically treat a mouth region of children, comprising a part intended to be positioned in the mouth, which part is provided with a dispensing container for an active agent and a shaft at one end, and having at least one aperture provided in said shaft which allows the entrance of saliva into the dispensing container and its exit therefrom, and a part to remain outside the mouth, comprising a hand held member, whereby a filler opening centrically opening towards the hand held member, is arranged in the area between both parts, wherein the hand held member and a cover of the filler opening, which cover is an integral part of the hand held member, are manufactured as one uniform unit with the rest of the administration device, wherein said at least one aperture opens to one of:

i) a position to come in direct contact with an erupting tooth, and ii) a position towards a labial surface of a front tooth of a child using same.

2. Administration device according to claim 1, wherein the filler opening of the dispensing container is wide, an edge thereof is bottle mouth shaped, and the cover of the filler opening is formed by an elastic cover cup which is connected to the administration device by means of a flexible joining strip, which cover cup can be snapped shut over a bulged edge of the filler opening.

3. Administration device according to claim 2, wherein the filler opening is outwardly widening in shape.

4. Administration device according to claim 1, wherein the cover is formed by a plug entering into the filler opening, being permanently connected to the administration device by means of a flexible joining strip, an outer surface of the plug-shaped cover being provided with a recess for a key in order to facilitate the opening of the cover.

5. Administration device according to claim 4, wherein the cover has mantle surfaces and the mantle surfaces and the filler opening are provided with cooperating ¼ threads.

6. Administration device according to claim 4, wherein the cover has mantle surfaces and the mantle surfaces and the filler opening are provided with a bayonet attachment.

7. Administration device according to claim 1, wherein the hand held member is ring shaped, and connected to the rest of the administration device at two points situated on opposing sides of the filler opening in a suitable distance from each other, the cover to close the filler opening being connected to sides of the ring-shaped hand held member by means of at least two closing shafts, arranged in a substantially V-shaped manner with respect to each other.

8. Administration device according to claim 7, wherein a gripping means is arranged in an area in which the closing shafts and the cover joins together, in order to facilitate opening and closing of the cover.

9. Administration device according to claim 7, wherein the sides of the ring-shaped hand held member are inwardly curved at the areas in which each closing shaft joins with the hand held member.

10. Administration device according to claim 7, wherein the cover is a plug entering the filler opening.

11. Administration device according to claim 7, wherein the cover has mantle surfaces and the mantle surfaces and the filler opening are provided with cooperating ¼ threads.

12. Administration device according to claim 7, wherein the cover has mantle surfaces and the mantle surfaces and the filler opening are provided with a bayonet attachment.

13. Administration device according to claim 1, wherein the administration device is a pacifier, whereby the part to be positioned in the mouth is formed of a perforated sucking piece, an interior of which forms a dispensing container, and a part remaining outside the mouth comprises a protecting plate provided with air holes.

14. Administration device according to claim 13, wherein the sucking piece is laterally flattening in shape, and a flattened shaft thereof is provided with four apertures, two of which face the upper jaw and two facing the lower jaw.

15. Administration device according to claim 13, wherein the dispensing pacifier is in its entirety molded of an elastic material.

16. Administration device according to claim 15, wherein the elastic material is selected from the group consisting of rubber, silicon or soft vinyl.

17. Administration device according to claim 1, wherein the part to be positioned in the mouth, comprises an oral screen intended to be held in a space between lips and teeth, which oral screen is provided with a dispensing container, arranged in a central region of the oral screen.

18. Administration device according to claim 17, wherein the apertures in the dispensing container which open towards an oral cavity, are located on an inner surface of the oral screen.

19. Administration device according to claim 18, wherein the administration device is manufactured of a strong teether material, and the bail of the hand held member thereof is molded suitable for chewing.

20. Administration device according to claim 19, wherein the plug-shaped cover of the dispensing container is arranged to enter into the dispensing container when the ring-shaped hand-held member is pressed from the sides.

* * * * *